(12) United States Patent
Lin et al.

(10) Patent No.: US 6,200,269 B1
(45) Date of Patent: Mar. 13, 2001

(54) FORWARD-SCANNING ULTRASOUND CATHETER PROBE

(75) Inventors: Gregory Sharat Lin, Fremont; Kenneth R. Erikson, Los Gatos, both of CA (US)

(73) Assignee: Diasonics, Ultrasound, Inc., Santa Clara, CA (US)

( * ) Notice: Subject to any disclaimer, the term of this patent is extended or adjusted under 35 U.S.C. 154(b) by 0 days.

(21) Appl. No.: 09/087,463

(22) Filed: May 28, 1998

(51) Int. Cl.[7] .................................................. A61B 8/12
(52) U.S. Cl. ................................... 600/466; 600/446
(58) Field of Search ..................................... 600/444, 445, 600/446, 462–467

(56) References Cited

U.S. PATENT DOCUMENTS

| | | | |
|---|---|---|---|
| 4,785,816 | * 11/1988 | Dow et al. ............................ | 600/446 |
| 5,373,845 | * 12/1994 | Gardineer et al. .................... | 600/467 |
| 5,373,849 | * 12/1994 | Maroney et al. ..................... | 600/463 |
| 5,377,685 | * 1/1995 | Kazi et al. ............................ | 600/463 |
| 5,505,088 | * 4/1996 | Chandraratna et al. ............. | 600/466 |
| 5,509,418 | * 4/1996 | Lum et al. ............................ | 600/463 |
| 5,701,901 | * 12/1997 | Lum et al. ............................ | 600/463 |

* cited by examiner

*Primary Examiner*—Francis J. Jaworski
(74) *Attorney, Agent, or Firm*—Blakely, Sokoloff, Taylor & Zafman LLP

(57) ABSTRACT

A forward-scanning ultrasound catheter probe. An ultrasound catheter probe includes a forward-scanning transducer positioned at the tip of the probe. As such, the forward-scanning transducer may provide images of structures that may lie ahead of the tip of the probe. Furthermore, the forward-scanning transducer is repositioned by a drive mechanism coupled to the front-scanning transducer to provide a sector scan. In one embodiment, a bimorph piezoelectric drive is utilized to sweep the forward-scanning transducer across an arc to provide an imaging area associated with a sector scan.

31 Claims, 7 Drawing Sheets

FORWARD-SCANNING ULTRASOUND CATHETER PROBE

BACKGROUND OF THE INVENTION

1. Field of the Invention

The invention relates to the field of ultrasound imaging devices which may be used, for example, for medical diagnosis. More particularly, the invention relates to ultrasound catheter probes.

2. Background Information

Various ultrasound techniques and devices have been developed for imaging the interior of a body (hereinafter, "body" refers to various types of subjects, such as humans, animals, non-living structures, etc.). One application of ultrasound imaging has been in the medical field, and in particular, in catheter probes. Such probes are typically used to diagnose lumen of bodies, such as blood vessels or other fluid carrying ducts. Such diagnosis is sometimes provided, at least in part, by generating ultrasound images of the lumen with ultrasound imaging devices installed within or about the catheter probe.

Conventional catheter probes for intraluminal ultrasound imaging typically perform circular ultrasound scanning within the lumen or within proximity to a plane that is perpendicular to the catheter probe and the lumen. As a result, such conventional catheter probes are generally limited in the field of view that may provide, especially with respect to imaging of structures that lie "ahead" of the catheter probe. For example, such conventional catheter probes cannot provide desired images of stenotic or obstructive lesions within blood vessels or other fluid ducts, for example, to determine size and/or morphology of such obstructions, without forcing the catheter probe through or past such lesions. Thus, ultrasound imaging of obstructive lesions, for example, may not be possible if the lumen becomes smaller than the catheter probe sheath or if a substantial portion of the lumen is obstructed.

Thus, what is desired is an ultrasound probe that provides improved imaging and/or access capabilities over prior devices and techniques.

SUMMARY OF THE INVENTION

The present invention provides a forward-scanning ultrasound catheter probe. According to one aspect, an ultrasound catheter probe includes a forward-scanning transducer positioned at the tip of the probe. As such, the forward-scanning transducer may provide images of structures that may lie ahead of the tip of the probe. Furthermore, the imaging area associated with the forward-scanning transducer may be varied by repositioning the transducer via a drive mechanism coupled to the front-scanning transducer. In one embodiment, a bimorph piezoelectric drive is utilized to sweep the front scanning transducer across a sector imaging area.

DETAILED DESCRIPTION

The present invention provides a forward-scanning ultrasound catheter probe. According to one aspect of the invention, the ultrasound catheter probe of the present invention includes a forward-scanning transducer positioned at the tip of the probe, which transducer may represent various types of transducers (including transducer arrays). In one embodiment of the invention, the forward-scanning transducer provides scanning of a sector imaging area. In one embodiment of the invention, a piezoelectric drive is utilized to move the transducer through different angles to sweep across the sector imaging area It will be appreciated that while the invention is primarily described herein with reference to medical catheter probes, the ultrasound imaging apparatuses and methods disclosed herein may be utilized in various other medical or non-medical applications without departing from the scope of the invention. Thus, the invention should not necessarily be limited to medical imaging devices and intraluminal catheter probes.

In the following description, numerous specific details are set forth to provide a thorough understanding of the invention. However, it is understood that the invention may be practiced without these specific details. In other instances, well-known circuits, structures and techniques have not been shown in detail to avoid obscuring the invention.

Figure 1A:
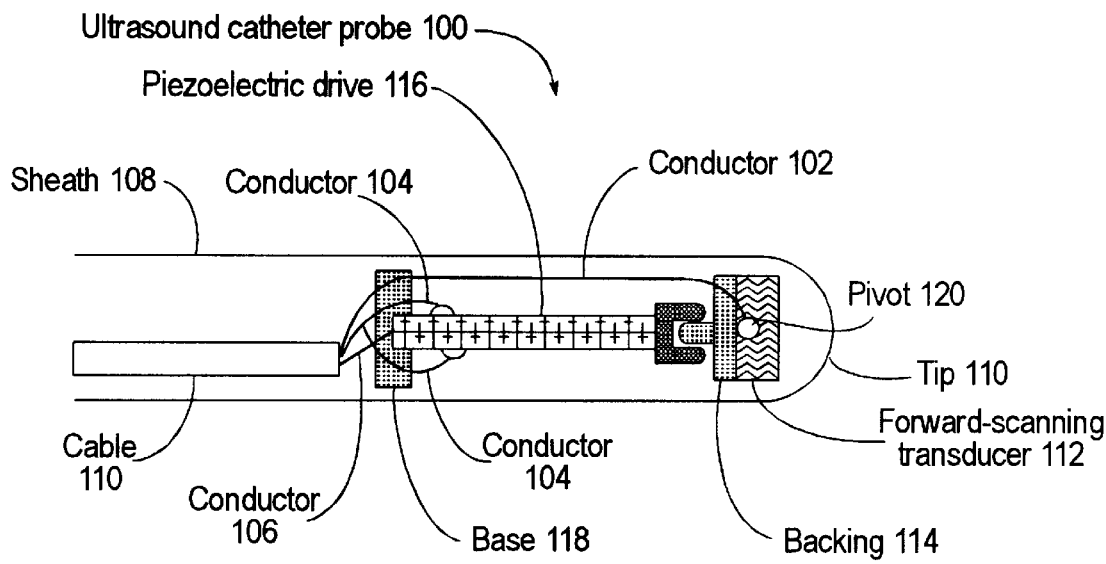
FIG. 1A is a diagram showing a longitudinal side view of the distal end of an ultrasound catheter probe, according to one embodiment of the invention.

FIG. 1A is a diagram showing a longitudinal side view of the distal end of an ultrasound catheter probe, according to one embodiment of the invention. The ultrasound catheter probe (probe) 100 shown in FIG. 1A is defined at a distal end by a tip 110. Furthermore, the probe 100 includes a sheath 108 that may enclose a number of elements, as described below and shown in the longitudinal and cross-sectional views of the probe 100. Positioned substantially at the tip 110 of the probe 100 is a forward-scanning transducer 112, which provides "end-fire" imaging from the tip 110. Accordingly, the forward-scanning transducer 112 may exchange ultrasound signals to provide a set of image information representing an image area associated with the area that is in front/ahead of the tip 110. It will be appreciated that the forward-scanning transducer 112 represents one or a combination of known types, shapes, and arrays of transducers. In one embodiment, the forward-scanning transducer 112 is implemented by an end-fire circular transducer.

In one embodiment, the forward-scanning transducer 112 includes a backing 114, which may represent one or a combination of known materials or devices for providing acoustic damping to the forward-scanning transducer 112, especially if/when the forward-scanning transducer is repositioned, as described below. In alternative embodiments, a backing is not necessarily utilized with the forward-scanning transducer 112.

The forward-scanning transducer 112, along with the (optional) backing 114, is attached to a pivot 120, which in turn is mechanically coupled to a drive which allows repositioning of the forward-scanning transducer 112 to sweep across (at least a portion of) an imaging area associated therewith. In one embodiment of the invention, for example, as shown in FIG. 1A, the drive is provided by a bimorph piezoelectric drive. A bimorph is generally comprised of a piezoelectric or thermomotive bilayer, in which one layer is induced (e.g., by electric or thermal energy) to expand, while the other layer is induced to contract As a result, the entire bilayer structure may be induced to curve to one side or another.

As shown in FIG. 1A, a piezoelectric drive 116 is mechanically coupled to the pivot 120 to allow scanning across the imaging area associated with the forward-scanning transducer 112 by incrementally changing the angle of the forward-scanning transducer 112 across an arc, thereby providing a sector scan. In one embodiment of the invention, the piezoelectric drive 116 is anchored by a base plate 118 and is electrically coupled to two or more conductive elements provided by a cable 110. In one embodiment, each of two conducting elements, shown by a conductor 104 and a conductor 106, is attached to one or more electrodes of the piezoelectric drive 116. The conductors 104 and 106 may represent a copper or other type of wire or electrical conductive element. In one embodiment, a bimorph or binary piezoelectric drive is utilized, which includes a center electrode and two outer electrodes, wherein each of the two outer electrodes is attached to the same or a different one of the conductors 104 and 106. By applying a voltage, which may be a stepped voltage ramp, to one or both of the outer electrodes, relative to the center electrode, the piezoelectric drive may undergo a piezoelectric effect (depicted in FIG. 1C) to cause the forward-scanning transducer 112 to be angled through an arc to transmit and receive ultrasound vectors in a sector scan. In one embodiment, the pivot 120 allows repositioning of the forward-scanning transducer 112 (e.g., through an arc). In one embodiment, the forward-scanning transducer 112 is incrementally angled through an arc to transmit and receive ultrasound vectors in a sector scan.

In alternative embodiments of the invention, other types of drives may be used to scan the imaging area provided by the forward-scanning transducer 112. For example, a thermomotive drive may be used in one embodiment, by coupling two or more materials having different thermal coefficients of expansion to the forward-scanning transducer 112 (or other component, such a backing, pivot, etc.). By providing heat, which may be provided via electrical resistance or other source, to the materials, such that one expands more relative to another, the forward-scanning transducer 112 may be repositioned (e.g., incrementally angled through an arc to transmit and receive ultrasound vectors in a sector scan).

Still, other types of drives may be used in alternative embodiments of the invention to reposition the forward-scanning transducer 112, for example, to provide a sector scan.

Figure 1B:
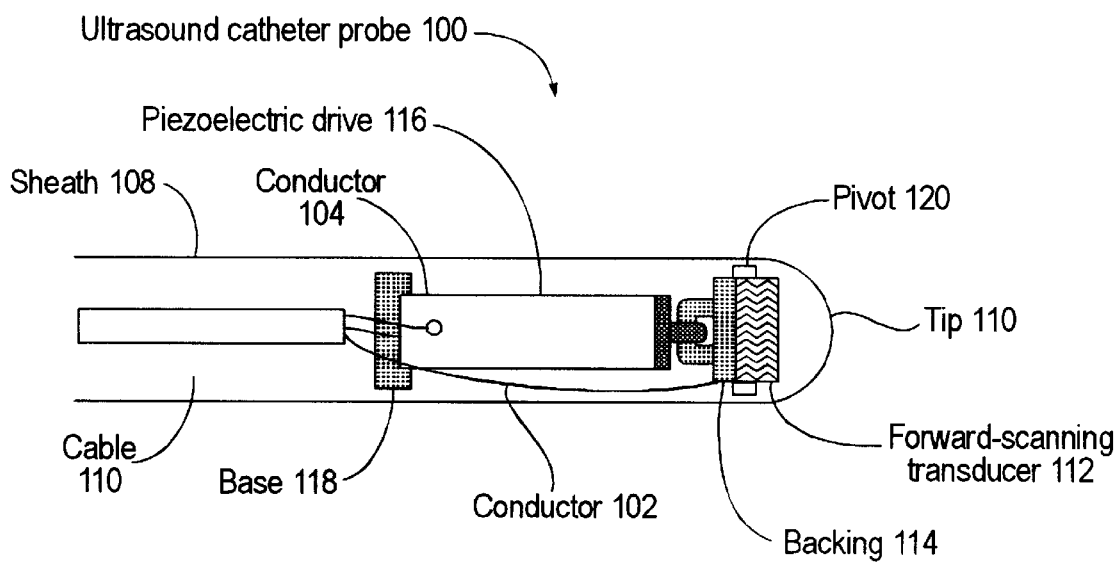
FIG. 1B is a diagram showing a longitudinal top view of the probe 100 of FIG. 1A, rotated 90 degrees with respect to the longitudinal side view shown in FIG. 1A.

FIG. 1B is a diagram showing a longitudinal top view of the probe 100 of FIG. 1A, rotated 90 degrees with respect to the longitudinal side view shown in FIG. 1A. As such, FIG. 1B shows the probe 100 described above with reference to FIG. 1A, while showing one possible connection of the conductors, such as the conductor 104, to an outer electrode of the piezoelectric drive 116.

Figure 1C:
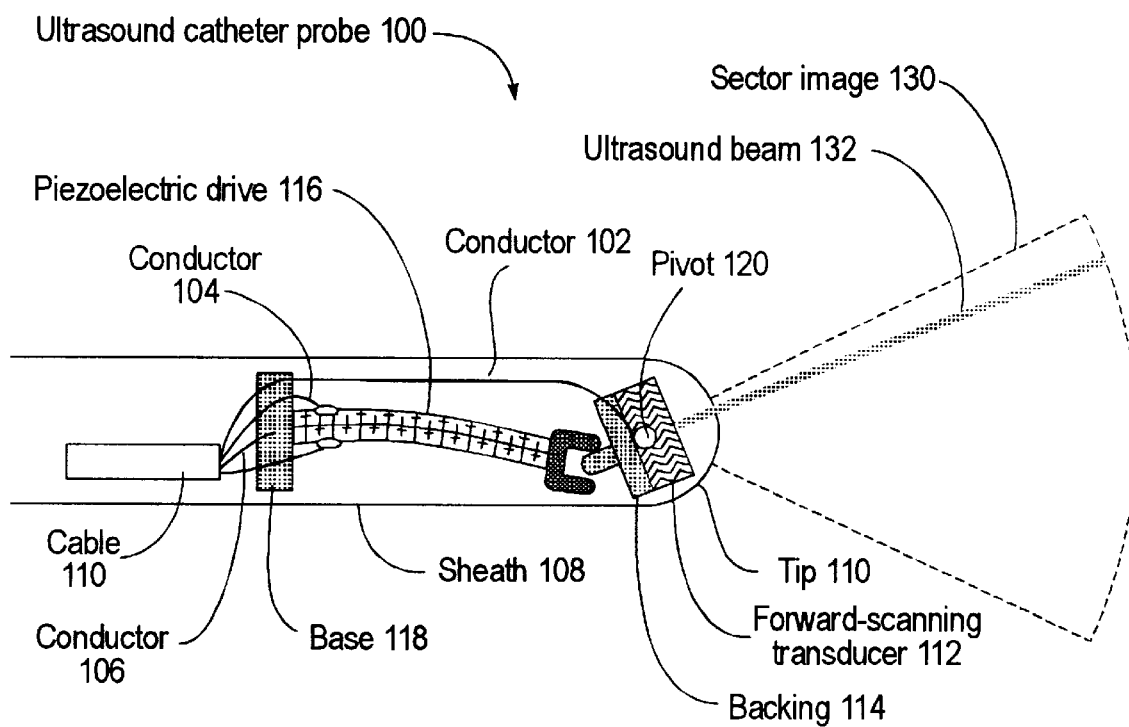
FIG. 1C is a diagram depicting the probe 100 of FIGS. 1A–1B in a mode of operation, according to one embodiment of the invention.

FIG. 1C is a diagram depicting the probe 100 of FIGS. 1A—1B in a mode of operation, according to one embodiment of the invention. As described above, the piezoelectric drive 116 represents a bimorph, which may be induced to curve, such that the forward-scanning transducer 112 is repositioned to provide a sector scan. Thus, FIG. 1C depicts the probe 100 described above with reference to FIGS. 1A–1B, in which the piezoelectric drive 116 is shown in a curved position. As a result, the forward-scanning transducer 112 is shown in a position associated with an ultrasound beam 132. By inducing the piezoelectric drive 116 to curve in other directions, which, in one embodiment is performed incrementally by applying an electric potential, for example, to the conductors 104 and 106 attached thereto, the forward-scanning transducer 112 may be repositioned about the pivot 120 to provide an imaging area shown by a sector image 130. It will be appreciated, however, that the sector image 130 is shown for illustrative purposes, and depending on various embodiments and implementations of the present invention, various sizes and shapes of imaging areas may be provided by repositioning of the forward-scanning transducer.

Figure 2A:
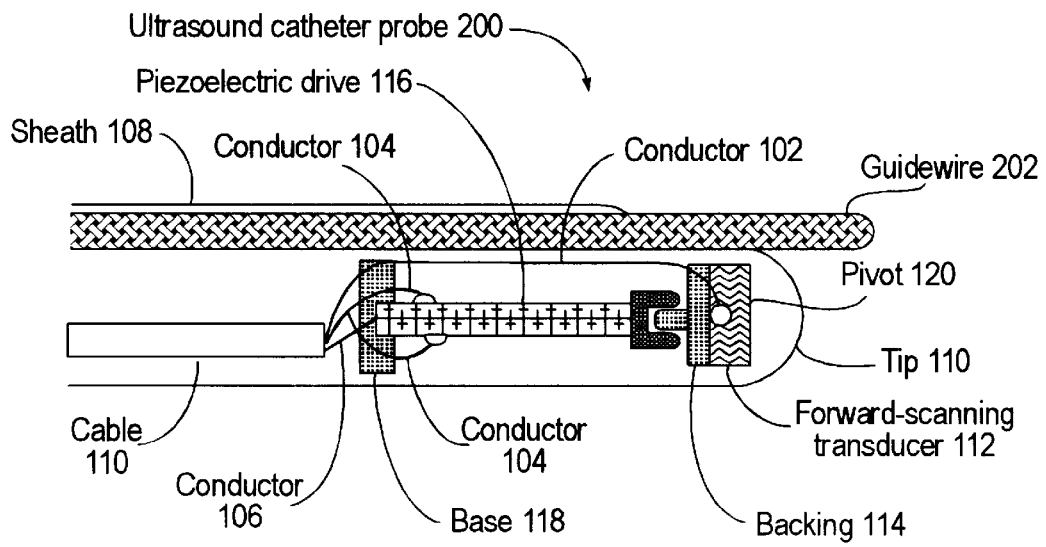
FIG. 2A is a diagram showing a longitudinal side view of the distal end of an ultrasound catheter probe having a guidewire inserted therein, according to one embodiment of the invention.

FIG. 2A is a diagram showing a longitudinal side view of the distal end of an ultrasound catheter probe having a guidewire inserted therein, according to one embodiment of the invention. The ultrasound catheter probe (probe) 200 shown in FIG. 2A may include several of the same elements as the probe 100 shown in FIGS. 1A–1B and described above, such as the piezoelectric drive 116 (which may be implemented, instead, as a thermomotive or other type of drive), the forward-scanning transducer 112, which may provide an end-fire sector scan, etc. In addition, the probe 200 includes a guidewire 202 which extends axially through the probe 200, and up to the tip 110 of the probe 200. In one embodiment, the guidewire 202 may extend beyond the tip 110. The guidewire 202 may be used as an instrument to perform one or more types of procedures, such as guiding the insertion of the catheter probe 200 into arteries and veins, or positioning the catheter probe tip 110 at a desired location within a body cavity or lumen.

Figure 2B:
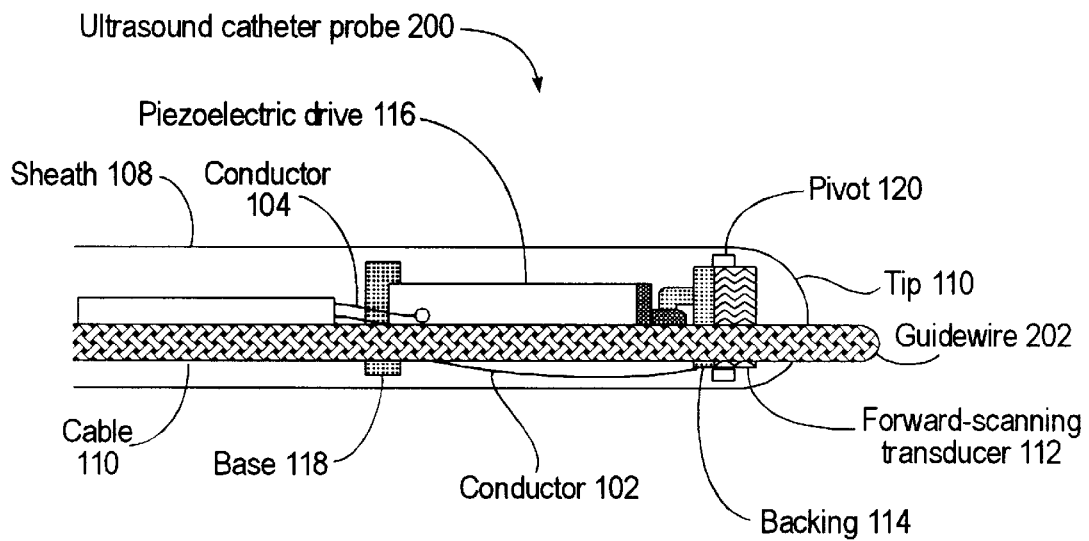
FIG. 2B is a diagram showing a longitudinal top view of the probe 200 of FIG. 2A, rotated 90 degrees with respect to the longitudinal side view shown in FIG. 2A.

FIG. 2B is a diagram showing a longitudinal top view of the probe 200 of FIG. 2A, rotated 90 degrees with respect to the longitudinal side view shown in FIG. 2A. As such, FIG. 2B may provide another view of the guidewire 202 with respect to other elements of the probe 200, such as an electrode of the piezoelectric drive 116.

Figure 2C:
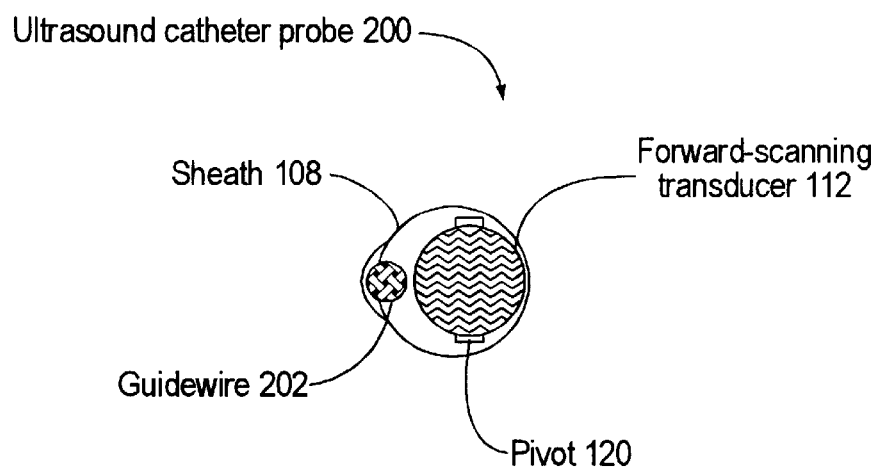
FIG. 2C is a diagram showing an end or transverse cross-sectional view of the probe 200 shown in FIGS. 2A–2B.

FIG. 2C is a diagram showing an end or transverse cross-sectional view of the probe 200 shown in FIGS. 2A–2B. As such, FIG. 2C shows one possible position for the guidewire 202 relative to the sheath of the probe 200. Of course, it will be appreciated by those in the art that other configurations for the guidewire 202 and/or other instruments that may be used with an ultrasound catheter probe of the present invention are possible.

Figure 3A:
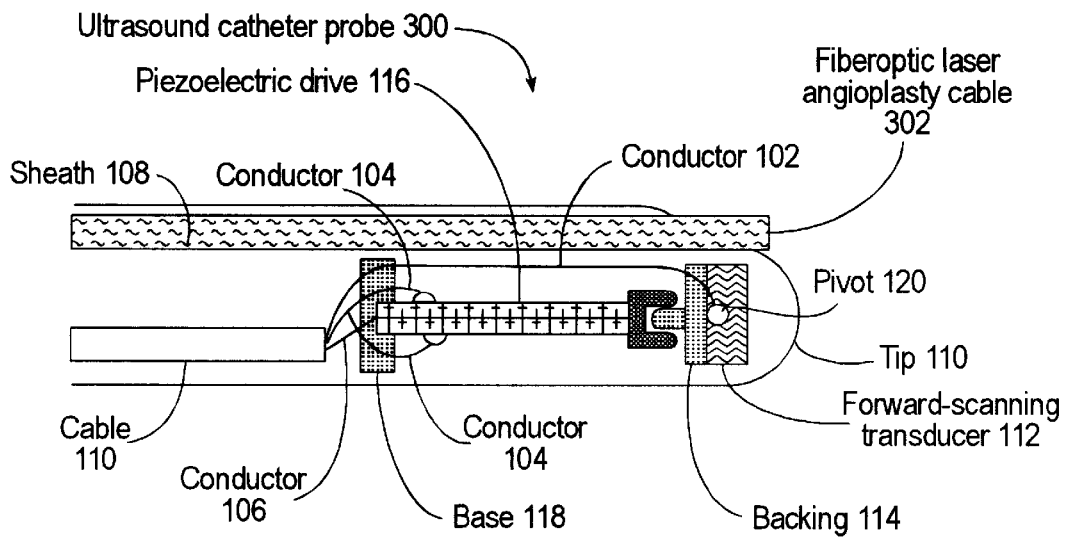
FIG. 3A is a diagram showing a longitudinal side view of the distal end of an ultrasound catheter probe having a fiberoptic laser angioplasty cable inserted therein, according to one embodiment of the invention.

FIG. 3A is a diagram showing a longitudinal side view of the distal end of an ultrasound catheter probe having a fiberoptic laser angioplasty cable inserted therein, according to one embodiment of the invention. The ultrasound catheter probe (probe) 300 shown in FIG. 3A may include several of the same elements as the probe 100 shown in FIGS. 1A–1B and described above, such as the piezoelectric drive 116 and the forward-scanning transducer 112, which may provide an end-fire sector scan, etc. In addition, the probe 300 includes a fiberoptic laser angioplasty cable 302 which extends axially through the probe 300, and up to the tip 110 of the probe 300. In one embodiment, the fiberoptic laser angioplasty cable 302 may extend beyond the tip 110. The fiberoptic laser angioplasty cable 302 may be used as an instrument to perform one or more types of procedures, such as intraluminal laser angioplasty. In one embodiment, the probe 300 may be used to treat atherosclerotic disease, including coronary artery disease, by enabling a user to view images of lesions that "lie ahead" of the tip 110 of the probe 300, and such lesions may be ablated by the fiberoptic laser angioplasty cable 302.

Figure 3B:
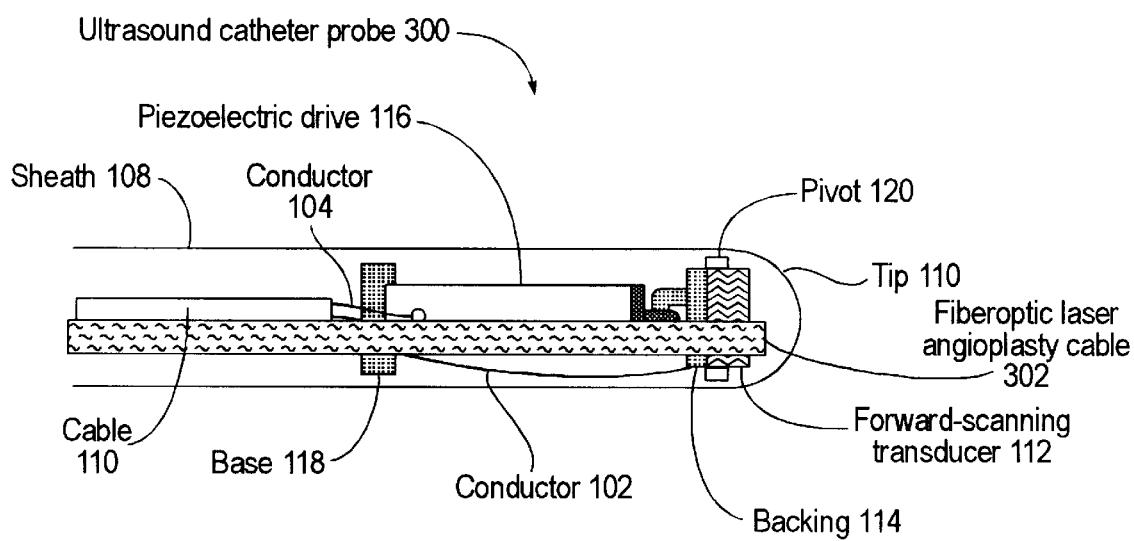
FIG. 3B is a diagram showing a longitudinal top view of the probe 300 of FIG. 3A, rotated 90 degrees with respect to the longitudinal side view shown in FIG. 3A.

FIG. 3B is a diagram showing a longitudinal top view of the probe 300 of FIG. 3A, rotated 90 degrees with respect to the longitudinal side view shown in FIG. 3A. As such, FIG. 3B may provide another view of the fiberoptic laser angioplasty cable 302 with respect to other elements of the probe 300, such as an electrode of the piezoelectric drive 116.

Figure 3C:
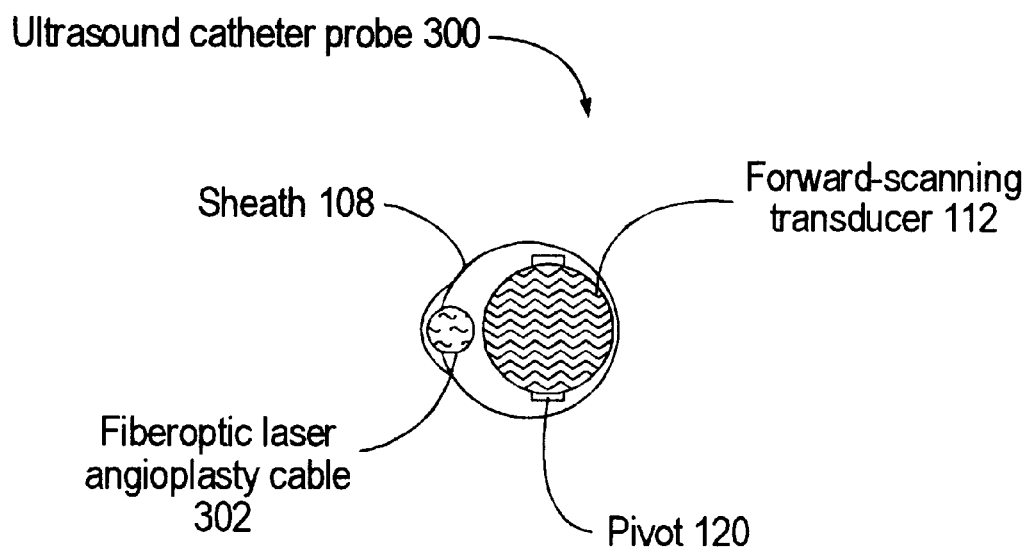
FIG. 3C is a diagram showing an end or transverse cross-sectional view of the probe 300 shown in FIGS. 3A–3B.

FIG. 3C is a diagram showing an end or transverse cross-sectional view of the probe 300 shown in FIGS. 3A–3B. As such, FIG. 2C shows one possible position for the fiberoptic laser angioplasty cable 302 relative to the sheath of the probe 300. Of course, it will be appreciated by those in the art that other configurations for the fiberoptic laser angioplasty cable 302 and/or other instruments that may be used with an ultrasound catheter probe of the present invention are possible.

Figure 4:
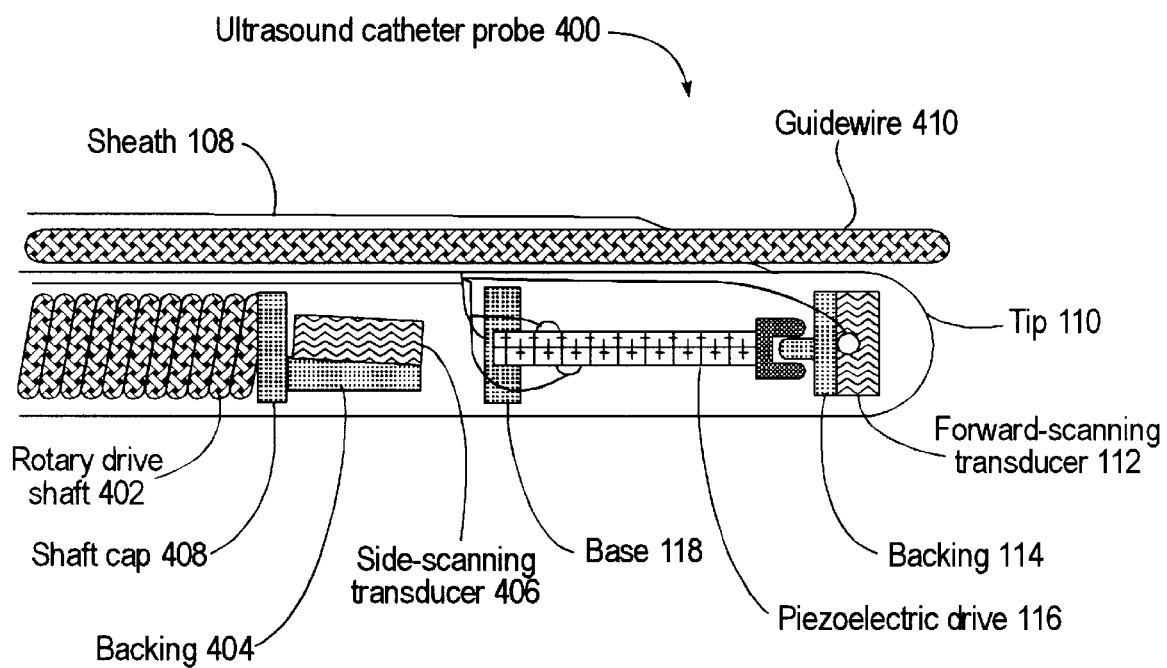
FIG. 4 is a diagram showing a longitudinal side view of the distal end of an ultrasound catheter probe that utilizes both a forward-scanning transducer and a rotating side-scanning transducer, according to one embodiment of the invention.

FIG. 4 is a diagram showing a longitudinal side view of the distal end of an ultrasound catheter probe that utilizes both a forward-scanning transducer and a rotating side-scanning transducer, according to one embodiment of the invention. In FIG. 4, an ultrasound catheter probe 400 is shown which may include some of the elements described above with reference to FIGS. 1–3, such as the piezoelectric drive 116 coupled to the forward-scanning transducer 112, which, in turn, is positioned substantially at the tip 110 of the probe 400.

In addition, the probe 400 includes a side-scanning transducer 406 positioned behind the forward-scanning transducer 112, relative to the tip of the probe 400. The side-scanning transducer 406 may be coupled to an acoustic damping backing 404, which in turn is coupled to a drive, which in the embodiment of FIG. 4 corresponds to a rotary drive shaft 402. The rotary drive shaft 402, in one embodiment, allows the side-scanning transducer 406 to be rotated about an axis of the probe 400 to generate radial-fire ultrasound beams, which could provide circular image information. It will be appreciated that various types of rotary drive shafts, such as those utilized in conventional side-scanning ultrasound catheter probes, may be used with the side-scanning transducer 406. By providing the combination of the forward-scanning transducer 112 and a side-scanning transducer, the probe 400 may provide greater imaging flexibility and capabilities, for example, in medical intraluninal ultrasound imaging applications.

In alternative embodiments, an ultrasound catheter probe of the present invention, including, for example, the probes 100, 200, 300, and 400 described above, may provide other imaging devices and functionality, such as 2D Doppler, etc.

Furthermore, while two instruments-namely, a guidewire and a fiberoptic laser angioplasty cable—which may be used with a probe of the present invention are described above, it will be appreciated that several other types of instruments (e.g., medical diagnostic instruments) may be used in conjunction with a probe of the present invention. In yet other embodiments, such as the one shown in FIGS. 1A–1B, an instrument may not necessarily be utilized with a probe of the present invention.

Furthermore, although not shown in the described figures, it will be appreciated that the present invention may typically be utilized with various types of known ultrasound and/or Doppler processing circuitry (e.g., digital signal processors, general purpose processors, storage devices/media to store data and/or routines, etc.) and imaging/display subsystems (e.g., displays, audio output devices, etc.).

ALTERNATIVE EMBODIMENTS

While the invention has been described in terms of several embodiments, those skilled in the art will recognize that the invention is not limited to the embodiments described. In particular, the invention can be practiced in several alternative embodiments that provide forward-scanning ultrasound catheter probes.

Therefore, it should be understood that the method and apparatus of the invention can be practiced with modification and alteration within the spirit and scope of the appended claims. The description is thus to be regarded as illustrative instead of limiting on the invention.

What is claimed is:

1. An ultrasound probe comprising:
   a distal end that defines a tip of said ultrasound probe;
   a forward-scanning transducer positioned at said tip of said ultrasound probe;
   a drive, coupled to said forward-scanning transducer, to sweep said forward-scanning transducer across a sector, said drive comprises a piezoelectric drive assembly; and
   a side-scanning transducer positioned behind said forward-scanning transducer, relative to said tip of said ultrasound probe.

2. The ultrasound probe of claim 1, further comprising:
   a sheath, defining a stem of said probe, said sheath enclosing said forward-scanning transducer and said drive.

3. The ultrasound probe of claim 2, further comprising:
   a base piece, coupled to said drive.

4. The ultrasound probe of claim 1, wherein said piezoelectric drive assembly comprises a first portion and a second portion, wherein at least one of said first and second portions is coupled to an electric conductor.

5. The ultrasound probe of claim 1, further comprising a power supply, coupled to said electric conductor, to generate a piezoelectric effect to change a position of said forward-scanning transducer to scan said sector.

6. The ultrasound probe of claim 1, further comprising an acoustic backing, coupled to said forward-scanning transducer.

7. The ultrasound probe of claim 1, further comprising a guidewire coupled to said probe.

8. The ultrasound probe of claim 1, further comprising a fiberoptic laser angioplasty cable coupled to said probe.

9. The ultrasound probe of claim 1, further comprising a rotary drive, coupled to said side-scanning transducer, to rotate said side-scanning transducer.

10. The ultrasound probe of claim 1, further comprising an acoustic backing, coupled to said side-scanning transducer.

11. The ultrasound probe of claim 1, wherein said drive comprises a thermomotive drive.

12. An ultrasound catheter probe comprising:
- a distal end that defines a tip of said ultrasound catheter probe;
- a pivot, positioned substantially at said tip of said ultrasound catheter probe;
- a forward-scanning transducer, coupled to said pivot;
- a piezoelectric drive, coupled to said pivot; and
- a side-scanning transducer coupled to said forward-scanning transducer, relative to said tip of said ultrasound catheter probe.

13. The ultrasound catheter probe of claim 12, further comprising:
- a sheath, defining a stem of said probe, said sheath enclosing said pivot, said forward-scanning transducer and said piezoelectric drive.

14. The ultrasound catheter probe of claim 12, further comprising:
- a base piece, coupled to said piezoelectric drive.

15. The ultrasound catheter probe of claim 12, wherein said piezoelectric drive comprises a first and a second layer to provide differential expansion and contraction, respectively, to curve said piezoelectric drive in response to an electrical voltage.

16. The ultrasound catheter probe of claim 12, wherein said piezoelectric drive assembly comprises a first portion and a second portion, wherein at least one of said first and second portions is coupled to an electric conductor.

17. The ultrasound catheter probe of claim 16, further comprising a power supply, coupled to said electric conductor, to provide a controlled piezoelectric effect that causes said pivot to move in a stepped manner to reposition said forward-scanning transducer to angularly scan across an arc to produce a sector imaging area.

18. The ultrasound catheter probe of claim 12, further comprising an acoustic damping backing, coupled to said forward-scanning transducer.

19. The ultrasound catheter probe of claim 12, further comprising a channel to accommodate a guidewire.

20. The ultrasound catheter probe of claim 12, further comprising a channel to accommodate a fiberoptic laser angioplasty cable.

21. The ultrasound catheter probe of claim 12, further comprising a rotary drive, coupled to said side-scanning transducer, to incrementally rotate said side-scanning transducer.

22. The ultrasound catheter probe of claim 12, further comprising an acoustic damping backing, coupled to said side-scanning transducer.

23. A method for providing ultrasound images from an ultrasound catheter probe, said method comprising:
- providing a forward-scanning transducer at a tip of said ultrasound catheter probe;
- repositioning said forward-scanning transducer to generate sector image information, said forward-scanning transducer to generate said sector image information comprises a piezoelectric driving force to move said forward-scanning transducer; and
- generating another set of image information based on signals from a side-scanning transducer included in said ultrasound catheter probe.

24. The method of claim 23, further comprising performing acoustic damping by providing an acoustic damping to said forward-scanning transducer.

25. The method of claim 23, further comprising guiding an instrument through a channel of said ultrasound catheter probe.

26. The method of claim 25, wherein said instrument comprises a fiberoptic laser angioplasty cable.

27. The method of claim 23, further comprising guiding positioning of said ultrasound catheter probe in a body by a guidewire.

28. The method of claim 23, further comprising repositioning said side-scanning transducer by a rotary drive, coupled to said side-scanning transducer.

29. The method of claim 28, wherein repositioning of said side-scanning transducer provides circular image information.

30. An ultrasound probe for providing ultrasound image information, said ultrasound probe comprising:
- a first means for providing forward-scanning from a tip of said ultrasound probe;
- a second means for repositioning said first means for providing a sector scan; and
- a third means for side-scanning transducer positioned behind said first means forward-scanning t, relative to said tip of said ultrasound probe.

31. The ultrasound probe of claim 30, further comprising a display means for providing images associated with said sector scan.

* * * * *